United States Patent [19]

Spangler et al.

[11] 4,378,499
[45] Mar. 29, 1983

[54] CHEMICAL CONVERSION FOR ION MOBILITY DETECTORS USING SURFACE INTERACTIONS

[75] Inventors: Glenn E. Spangler, Lutherville; Donald N. Campbell, Timonium; Stanley Seeb, Baltimore, all of Md.

[73] Assignee: The Bendix Corporation, Southfield, Mich.

[21] Appl. No.: 249,559

[22] Filed: Mar. 31, 1981

[51] Int. Cl.³ .............................................. H01J 49/40
[52] U.S. Cl. .................................... 250/287; 250/286; 250/288; 250/281
[58] Field of Search ............... 250/286, 287, 288, 281, 250/283; 422/98

[56] References Cited

U.S. PATENT DOCUMENTS 1,880,333 10/1932 Spindler .............................. 250/504
3,626,180 12/1971 Carroll et al. ....................... 250/287
3,697,748 10/1972 Cohen .................................. 250/288
4,311,669 1/1982 Spangler ............................. 422/98

Primary Examiner—Bruce C. Anderson
Assistant Examiner—Jack I. Berman
Attorney, Agent, or Firm—Bruce L. Lamb; W. G. Christoforo

[57] ABSTRACT

An ion mobility detector in which selectivity and sensitivity is enhanced by converting through surface interactions sample gas or vapor to a form more readily ionized or by converting through surface interactions interferent gas or vapor to a form less readily ionized. To accomplish the conversion, samples may be passed through a catalytically reactive filter prior to injection into the detector reaction region; exposed to a reactive coating placed on the surface of a permeable membrane prior to diffusion therethrough into the reaction region or exposed to a reactive coating placed on the interior walls of the reaction region.

8 Claims, 5 Drawing Figures

CHEMICAL CONVERSION FOR ION MOBILITY DETECTORS USING SURFACE INTERACTIONS

The present invention relates in general to ion mobility detectors and more specifically to means for improving sensitivity and specificity thereof through the use of surface interactions to convert sampled vapor to a form susceptible to ionization.

Ion mobility detectors are the primary instruments used in the field of plasma chromatography. Generally, the operation of an ion mobility detector is similar to the operation of a time of flight mass spectrometer, the obvious difference being that a time of flight mass spectrometer operates in a vacuum where the mean free path of the contained gases is many times the dimensions of the gas container, while the ion mobility detector operates generally at atmospheric pressure where the mean free path of the contained gases is a small fraction of the dimensions of the container. More particularly, a typical ion mobility detector is comprised of a combined ionization source and an ion reaction region, an ion drift region and an ion injection shutter or grid interposed between the ion reaction region and the ion drift region. A carrier gas, normally purified air or nitrogen, transports sample vapor of a material whose identity is to be characterized into the ion reaction region so that the gaseous mixture is exposed to the ionization source. Portions of both the carrier gas and the sample are directly ionized by the ionization source. However, as known to those practicing in this art, the characteristics of the carrier gas and the sample are usually such that the molecules of the carrier gas are more easily directly ionized by the ionization source than are the molecules of the sample. Since the mean free path of the carrier gas and sample is many times smaller than the dimensions of the reaction region there are multiple collisions between the molecules of the carrier and sample gases. As also known to those skilled in the art, the tendency of these collisions is to transfer the ion charge from the carrier molecules to the sample molecules, thereby ionizing the sample gas mainly by this secondary ionization process.

The charged particles or ions, derived from both the sample and carrier gas, are accelerated to a terminal velocity under the influence of an electrostatic field gradient within the reaction region toward an ion injection grid which, as mentioned earlier, separates the reaction region from the drift region. The grid is normally electrically biased to prevent the transfer of ions from the reaction region to the drift region. Periodically, the grid is deenergized for a short time period to permit a pulse of ions to pass therethrough into the drift region. Here, the ions, under the influence of an electrostatic drift field are drawn to an electrometer detector which terminates the drift region. The time arrival of each ion at the electrometer detector, relative to the time the grid was opened, is determined by the ion's mobility through the non-ionized drift gas occupying the drift region. The heavier ions characteristically move more slowly through the drift region and arrive at the electrometer detector with longer drift times than lighter ions. It is thus possible to characterize the ions and hence, the sample, by observing the time between the opening of the grid and the arrival of ions at the electrometer detector.

In a practical sense, an ion mobility detector may be used to determine whether a certain sample is present in an environment, such as a certain containment in atmospheric air. In this case ambient air is injected or drawn into the reaction region to react with carrier gas ions formed therein by the ionization source. The electrometer detector is sampled at predetermined times after the grid is opened, corresponding to the mobility of the containment ions, to discover whether pulses of ions are then arriving at the electrometer detector. If electric current is measured then it can be concluded that the containment is present.

Several problems are encountered when using ion mobility detectors for environmental sampling purposes. A first problem involves no alarms due to interferences from the normal composition (e.g. oxygen, water, ammonia and/or nitrogen oxides) of the ambient air being drawn into the reaction region of the detector cell. The second involves false alarms or no alarms due to interferences from extraneous vapor components contained in the ambient air being drawn into the reactor region of the detector cell.

The first problem is associated with the principles underlying the tendency of a charge residing on a reactant ion to transfer to a neutral sample molecule. The transfer of the charge is necessary if a product ion is to be formed from the sample molecule and the sample molecules are to be detected. As is known to those skilled in the art, this tendency to transfer charge is related to the relative proton and/or electron affinities of the ions and molecules present in the reactor region either due to composition of the carrier gas or to products of the ionization process. For example, if ammonia with a relatively high (202.3 Kcal/mole) proton affinity is used to produce ammonium ($NH_4$) reactant ions, charge (proton) transfer from the ammonium reactant ion to dimethylsulfide could not be accomplished unless the proton affinity of 197.6 Kcal/mole for dimethylsulfide could be increased to 208.2 Kcal/mole through the oxidation of dimethylsulfide to dimethylsulfoxide. Since ambient air is primarily a source of ammonium reactant ions in ion mobility detectors, dimethylsulfide could not be detected in ambient air unless it was oxidized to dimethylsulfoxide. The same considerations supply to the hydrolysis of alkanes or alkyl halides to alcohols when the hydronium ($H_3O^+$) ion is used as the major reactant ion.

The second problem is associated with the tendency of a charge to transfer from the reactant ion to extraneous components in the ambient atmosphere either having proton or electron affinities greater than that for the desired sample molecules or ion mobilities similar to the sample molecules of interest. That is, if the environmental sample contains one or more extraneous components whose ion charge is the same as or whose proton affinity is greater than that of the sample it is desired to detect, then ions of the extraneous components will be observed as interferents in preference to the sample molecule. Also, if the environmental sample contains one or more extraneous components whose ion charge is the same as and whose ion mobility is similar to that of the sample it is desired to detect, then ions of the extraneous components will be observed as interferents arriving at the electrometer detector at such a drift time as to indicate the looked-for sample is present when in fact it may not be. An aggravated example of this problem is the tendency of the normal alkanes to cluster into molecules or ions of larger mass as well as to decompose into ions of lower mass so that the electrometer detector senses the arrival of ions with a wide range of drift times. That is, irrespective of the drift time for the sample molecule, an ion is formed from the normal alkanes whose mobility approximates that of the looked-for sample molecule. This leads to a false indication or alarm as described above. Therefore, another aspect of the invention is that of chemically converting the interferent molecules through surface interactions to molecular species with proton or electron affinities less than the sample and reactant ions, whereby interferences can be removed from detector response.

It is an object of the present invention to provide means for improving the sensitivity and specificity of ion mobility detectors for particular sample gases or vapors by converting those samples to species more readily ionized in the reaction region of the detector.

It is likewise an object of the invention to provide means for improving the sensitivity and selectivity of the ion mobility detectors by reducing the effects of interferent ions through converting interferent ions to a form less susceptible to ionization in the reaction region of the detector.

A further object of the invention, correlative to the foregoing, is to provide surface interactions for treating sample gases or mixtures of sample and carrier gases prior to the introduction thereof into the reaction region of an ion mobility detector whereby such gases may be converted to forms or species more readily ionizable, or less readily ionizable, as may be needed to maintain distinction at the detector output.

Briefly, the improved ion mobility detector of the invention uses surface interactions to alter the chemical structure of sample or interferent molecules so that their respective charge affinities are adjusted in such a manner to allow specific detection of sample molecules in the presence of interferent molecules. Neutral sample or interferent molecules are impinged on reactive surfaces to accomplish physical or chemical conversion. The surfaces may be metals, metal oxides, surface coatings, etc. which may be heated or illuminated by optical irradiation (primarily in the ultraviolet) to activate reactions.

Several embodiments of the invention are described. Conversion may be accomplished in a reactive filter through which sample and carrier gases are passed prior to introduction into the detector ionization and reaction region. In another embodiment of the invention a reactive coating is applied to the surface of a permeable membrane separating sample gas from carrier gas for conversion of sample or interferent prior to mixture with the carrier and introduction to the reaction region of the detector. In a third embodiment a reactive surface is positioned at the inlet of the detector ionization and reaction chamber so that the entering sample and carrier gas mixture will strike the reactive surface and undergo tailored reactions. In a fourth embodiment reactive coatings are disposed on the walls of the chambers of the reaction region and, in certain instances, the drift region.

In the drawings:

FIG. 1 illustrates a first embodiment of the invention. A sample gas mixed with a carrier gas is injected into the inlet of a reactive filter 10.

Figure 1:
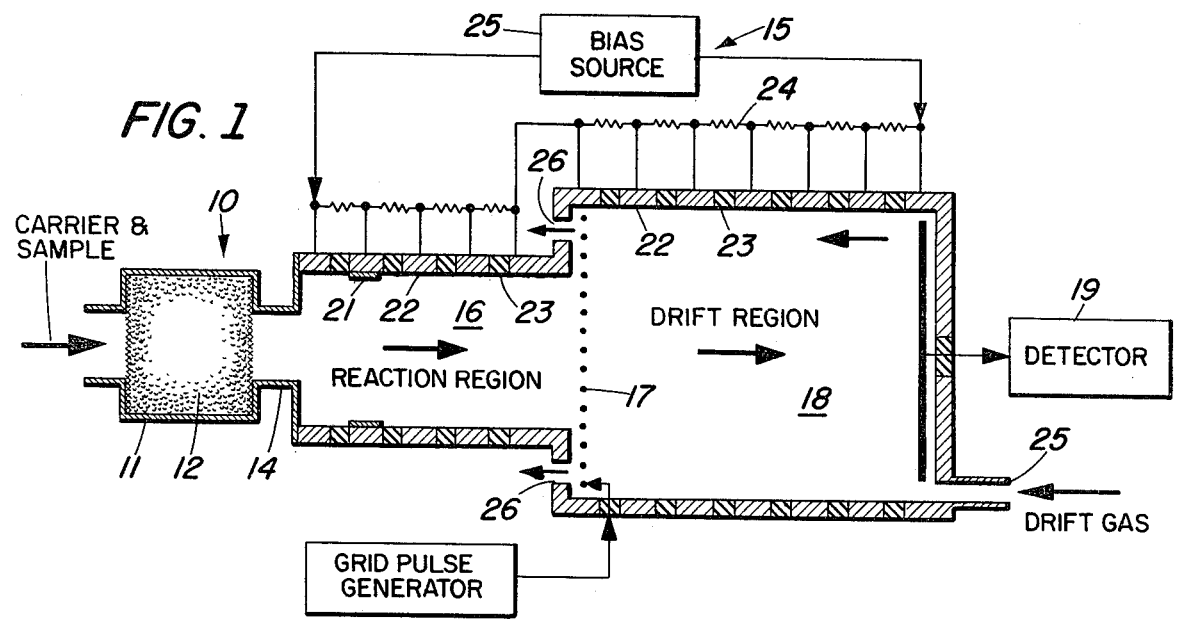
FIG. 1 is a diagrammatic sectional view of a first embodiment of the invention wherein a reactive filter is incorporated in the inlet to the ion mobility detector.

The sample or interferent molecules modified by the filter pass directly from the output of filter 10 to the inlet 14 of an ion mobility detector 15 of conventional design. The ion mobility detector includes a reaction region 16, an ion shutter grid 17, a drift region 18 and an electrometer detector 19. A radioactive ionization source 21 located at the inlet to the reaction region 16 directly ionizes a portion of the gases flow therethrough and such ions and the more numerous secondary ions generated by collisions in the reaction region are accelerated towards the ion shutter grid 17 by an electrical potential gradient existing in the reactive region. The potential gradients existing in both reaction region 16 and drift region 18 are established by forming the housings defining the reaction and drift regions of a plurality of conductive rings 22 separated from one another and secured into unitary cylindrical bodies by a plurality of insulating rings 23. A voltage divider 24 connected across the output of a high voltage bias source 25 applies progressively increasing voltages to the conductive rings 22 thereby creating the accelerating fields.

The ions generated in the reaction region and accelerated towards the drift region by the electric field are blocked from leaving the reaction region by the ion shutter grid 17 which carries a bias potential of like polarity to the accelerating ions. Periodically the repelling bias of shutter grid 17 is gated off and a burst of ions from the reaction region is permitted to enter the drift region. Within the drift region, ions accelerated towards the detector 19 by the electric field therein move counter to the stream of a non-reactive drift gas injected into port 25 and exhausted through ports 26. Ions of different molecules attain different terminal velocities, inversely related to their mass, so that the presence of molecules of a particular sample can be determined by sampling the detector output at predetermined times after gating of the shutter grid.

Filter 10 comprises a housing 11 packed with granular material 12 which may be composed of homogeneous reactive particles or heterogeneous reactive particles consisting of an inert support covered by a reactive coating. For example, the homogeneous particles can be metal filings and the heterogeneous particles can be alumina or diatomaceous earth pellets coated with a metallic acid, metal oxide or gel. Tungstic acid is particularly suited as an heterogeneous catalyst for the oxidation of sulfide compounds to their sulfone forms and silver fluoride salts are particularly suited for halogenating organophosphorous compounds. As sample or interferent molecules are drawn through the filter by the carrier gas, they collide with the filter packing to initiate the surface reaction. After completion of the surface reaction, the modified molecule is released by the surface to be carried into the ion mobility detector for ionization. The filter can be designed to allow conversion of sample molecules to a more ionizable form or to allow conversion of interferent molecules to a less ionizable form. A more complicated filter packing provides a mixture of reactive particles in the filter to allow detection of multiple samples or rejection of multiple interferents.

Figure 2:
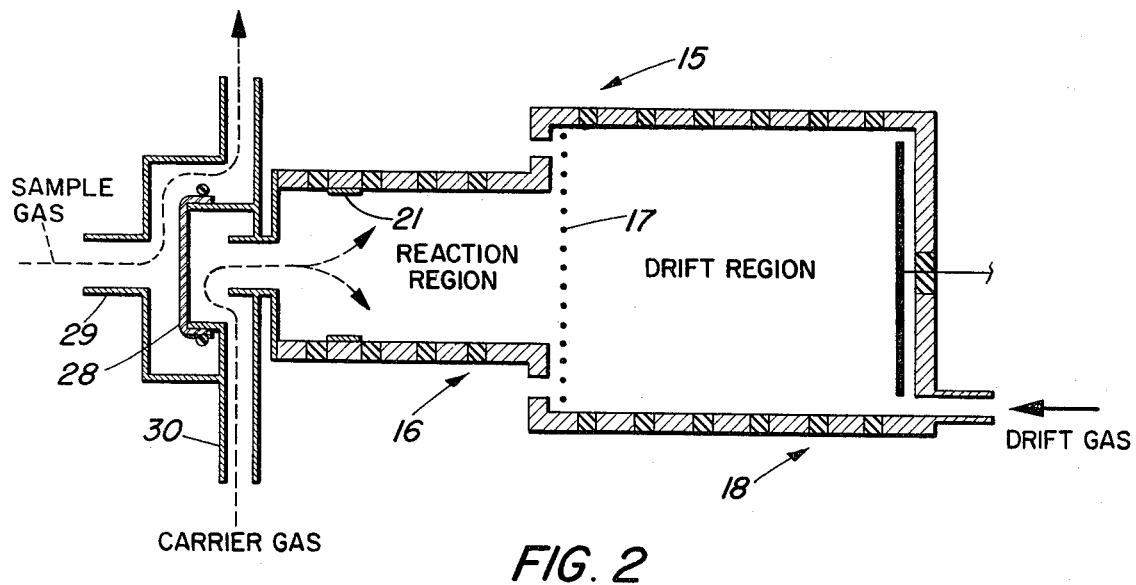
FIG. 2 is a diagrammatic sectional view of a second embodiment of the invention wherein a reactive coating is disposed on a permeable membrane separating sample gas from carrier gas at the inlet to the ionization and reaction chamber of an ion mobility detector.

A second embodiment of the invention is shown in FIG. 2. A membrane 28 is provided across the inlet of the ion mobility detector 15 as detailed in U.S. patent application Ser. No. 180,219, filed Aug. 21, 1980 by Glenn E. Spangler for "Membrane Interface for Ion Mobility Detector Cells". Coated on the membrane is a gel which can react with the sample or interferent molecules to produce a molecular species compatible with the detection scheme. As sample or interferent molecules are drawn through the inlet 29 onto the upstream surface of the membrane 28, they collide with the membrane to either adsorb and react, adsorb and not react, or not adsorb. The membrane coating can be selected to allow specific adsorption and reaction of sample molecules to enhance ionization for the ion mobility detector and to prohibit adsorption and reaction of interferent molecules so as to limit ionization by the ion mobility detector. For example, if it is desired to selectively detect organophosphorous compounds, 1-n-dodecyl-3-hydroximinomethyl pyridinium iodide (3-PAD) coatings are particularly suited for the selective adsorption and reaction, possibly hydrolysis, with these compounds. After reaction the molecules escape the downstream surface of the membrane to be carried by a carrier gas injected through port 30 into the reaction region 16 of the ion mobility detector for ionization purposes. For detection of multiple samples or rejection of multiple interferents the membrane can be zonally coated with different reactive gels or a multi-layer membrane, each layer of which is coated with a different reactive gel can be used.

Figure 3:
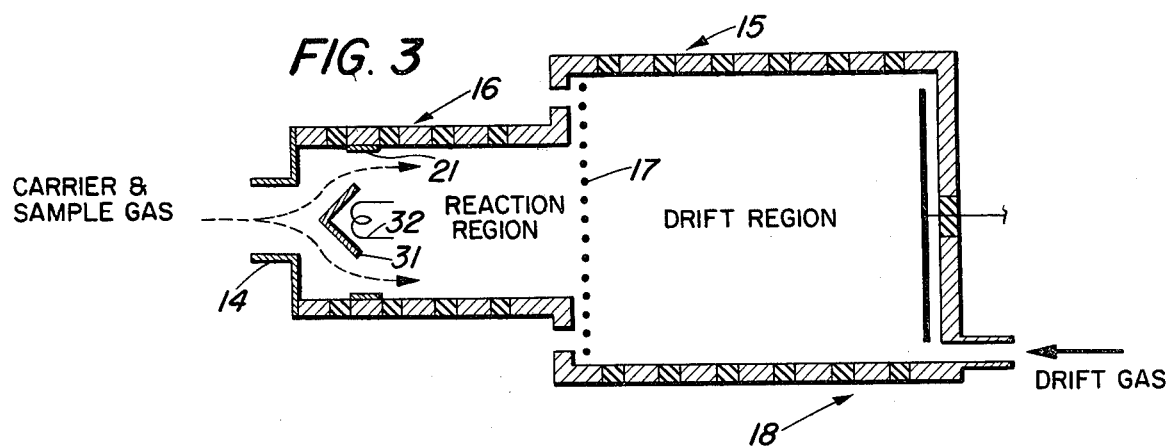
FIGS. 3 and 4 are diagrammatic sectional views of third embodiments of the invention wherein a reactive surface positioned at the inlet to the ionization detector is activated by heating or by irradiation.
Figure 4:
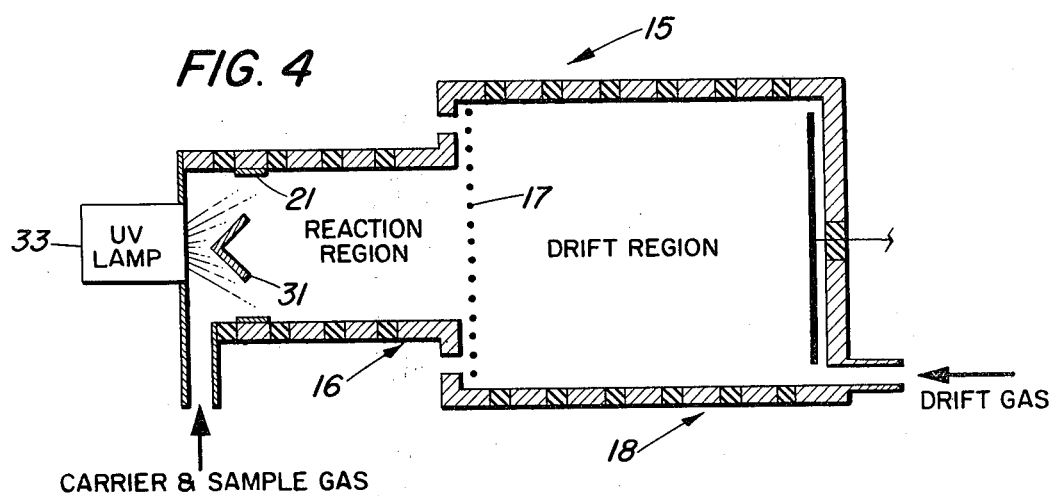

A third embodiment of the invention is illustrated in FIGS. 3 and 4. A reaction surface 31 is provided just behind the inlet 14 of the ion mobility detector so that sample or interferent molecules entrained in the carrier gas strike the surface and undergo surface reactions. The surface may be an exposed metal such as stainless steel, nickel or platinum to accomplish catalytic reactions or a coated surface to accomplish tailored reactions. The surface 31 is activated by radiant heat from an electrical heating element 32. In an alternative form, the surface 31 may be formed as a filament and an electrical current supplied directly thereto provides direct resistance heating. In the modification of FIG. 4, the surface 31 is activated by irradiation from an ultraviolet source 33. After completion of the surface reaction, the modified molecules escape the surface and are carried into the ion mobility detector for ionization. The surface or coating can be selected to provide conversion of sample molecules to a more ionizable form or to provide conversion of interferent molecules to a less ionizable form.

Figure 5:
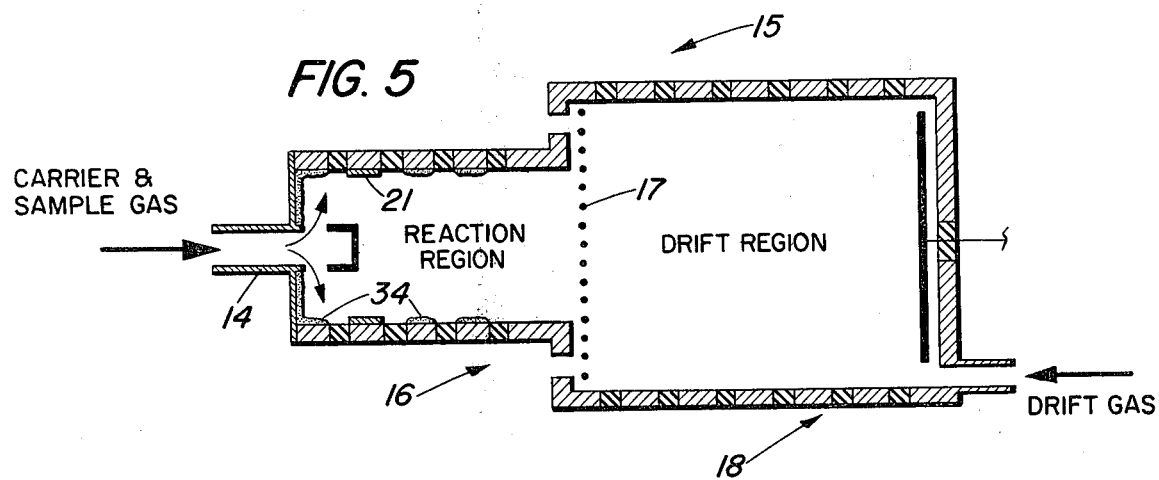
FIG. 5 is a diagrammatic sectional view of a fourth embodiment of the invention wherein a reactive coating is supported by the walls of the ion mobility detector reaction and drift chambers.

A fourth embodiment of the invention is shown in FIG. 5. A reactive coating 34 is applied to the internal wall of the reaction region 16 of the ion mobility detector 15. A diffuser 35 is positioned inside the inlet 14 to direct the flow of sample and carrier gases toward the coated wall 34. The coating 34 may be applied in a uniform pattern or it may be composed of different reactive substances applied in a zonal pattern. The coating can be selected to provide conversion of sample molecules to a more ionizable form or to provide conversion of interferent molecules to a less ionizable form.

The particular embodiment selected for utilization of the invention is dependent on the physical/chemical properties of the molecular compounds analyzed. For instance, if either the sample compound or its modified form is very susceptible to adsorptive losses, the packed filter embodiment of FIG. 1 is less desirable than the exposed surface embodiments of FIGS. 2-5. On the other hand, if the reaction rates for the surface interactions are slow, the larger surface area of the filter embodiment of FIG. 1 is preferred to the exposed surface areas of the FIGS. 2-5 embodiments. For the embodiments of FIGS. 1, 2 and 5, the possibility exists of increasing reaction rates by adding heat to the surfaces or, for FIGS. 2 and 5, by illuminating the surface with ultraviolet light.

The invention claimed is:

1. In an ion mobility detector including a chamber defining a reaction region and a drift region, an ion shutter grid separating said reaction region from said drift region, an ionization source in said reaction region, means furnishing sample gas, means furnishing carrier gas for transporting said sample gas to said reaction region and for ionizing said sample gas in said reaction region by secondary ionization, means furnishing drift gas to said drift region and a detector in said drift region,
    means for improving the sensitivity and selectivity of said ion mobility detector comprising,
    a catalytically reactive surface for treating gases undergoing ionization reactions in said reaction region, said surface causing an alteration in the ionization reaction chemistry of said gases whereby discrimination of molecules of said altered gases from molecules of unaltered gases at said detector is increased.

2. The improvement of claim 1 wherein said reactive surface comprises a filter packed with catalytically reactive granules and at least one of said carrier and sample gases are caused to flow through said filter prior to entry into said reaction region to cause alteration of the proton or electron affinity of said gas flowing through said filter.

3. The improvement of claim 2 wherein said reactive granules comprise granules of an inert material coated with a catalytically reactive substance.

4. The improvement of claim 1 wherein said reactive surface comprises a surface positioned at the inlet to said reaction region so as to be impinged upon by gases entering said reaction region and means for heating said surface to activate the same catalytically.

5. The improvement of claim 1 wherein said reactive surface comprises a surface positioned at the inlet to said reaction region so as to be impinged upon by gases entering said region and means for irradiating said surface to activate the same catalytically.

6. The improvement of claim 1 wherein said reactive surface comprises a catalytically reactive substance coated on the inner wall of said chamber defining said reaction region.

7. The improvement of claim 6, with additionally, means for diverting the flow of gases entering said reaction region to cause impingement of said gases upon said reactive substance.

8. In an ion mobility detector including a chamber defining a reaction region and a drift region, an ion shutter grid separating said reaction region from said drift region, an ionization source in said reaction region, a detector in said drive region, means furnishing drift gas to said drift region, means at the inlet to said reaction region for introducing carrier gas and sample vapor thereinto including a permeable membrane through which sample vapor is diffused prior to mixture with carrier gas, said carrier gas serving to transport said sample vapor in said reaction region and to provide ions of said sample vapor by secondary ionization; means for improving the selectivity and sensitivity of said ion mobility detector comprising, a catalytically reactive substance coated on said permeable membrane for altering by surface interactions the chemical identity of vapor diffusing therethrough whereby discrimination of molecules of said altered vapor from molecules of unaltered vapors at said detector is accomplished by the ionization reaction chemistry.

* * * * *